US005630882A

United States Patent [19]

de Miniac

[11] Patent Number: 5,630,882

[45] Date of Patent: May 20, 1997

[54] USE OF POLYETHER IONOPHORE ANTIBIOTICS TO CONTROL BACTERIAL GROWTH IN SUGAR PRODUCTION

[75] Inventor: Michel de Miniac, Paris, France

[73] Assignee: Union Nationale Des Groupements De Distallateurs D'Alcool (Ungda), Paris, France

[21] Appl. No.: 433,492

[22] PCT Filed: Nov. 4, 1993

[86] PCT No.: PCT/FR93/01089

§ 371 Date: May 5, 1995

§ 102(e) Date: May 5, 1995

[87] PCT Pub. No.: WO94/10862

PCT Pub. Date: May 26, 1994

[30] Foreign Application Priority Data

Nov. 6, 1992 [FR] France .................................. 92 13389

[51] Int. Cl.[6] .............................. C08B 30/12; C13J 1/06; C12N 1/20; C12P 17/18

[52] U.S. Cl. ............................ 127/32; 127/42; 127/46.1; 127/48; 435/119; 435/886

[58] Field of Search .............................. 127/32, 42, 46.1, 127/48; 435/119, 886

[56] References Cited

U.S. PATENT DOCUMENTS

| | | | |
|---|---|---|---|
| 3,734,773 | 5/1973 | Haley | 127/48 |
| 4,111,714 | 9/1978 | Hippchen et al. | 127/48 |
| 4,394,377 | 7/1983 | Spires | 424/177 |
| 4,547,523 | 10/1985 | Celmer et al. | 514/375 |
| 4,652,523 | 3/1987 | Celmer et al. | 435/119 |
| 4,795,494 | 1/1989 | Toth et al. | 127/48 |
| 5,320,681 | 6/1994 | Moc et al. | 127/48 |

FOREIGN PATENT DOCUMENTS

| | | | |
|---|---|---|---|
| 0171628 | 2/1986 | European Pat. Off. | A23K 1/17 |

*Primary Examiner*—Glenn A. Caldarola
*Assistant Examiner*—Patricia L. Hailey
*Attorney, Agent, or Firm*—Banner & Witcoff, Ltd.

[57] ABSTRACT

Method for producing sugar, characterized in that a polyether ionophore antibiotic is used to suppress gram positive bacteria growth during the process.

11 Claims, 1 Drawing Sheet

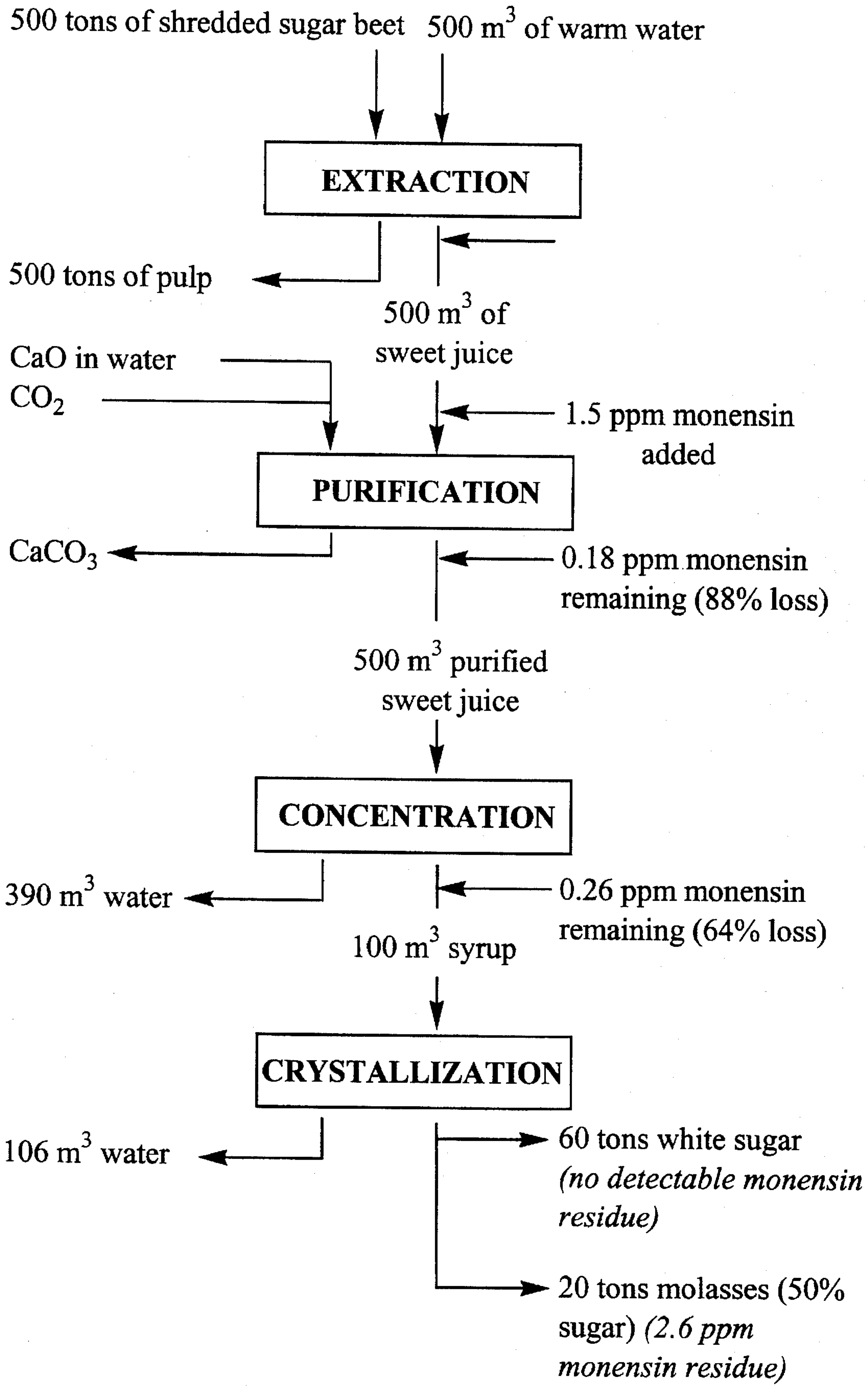
500 tons of shredded sugar beet
500 m3 of warm water
EXTRACTION
500 tons of pulp
500 m3 of sweet juice
CaO in water
CO2
1.5 ppm monensin added
PURIFICATION
CaCO3
0.18 ppm monensin remaining (88% loss)
500 m3 purified sweet juice
CONCENTRATION
390 m3 water
0.26 ppm monensin remaining (64% loss)
100 m3 syrup
CRYSTALLIZATION
106 m3 water
60 tons white sugar (no detectable monensin residue)
20 tons molasses (50% sugar) (2.6 ppm monensin residue)

USE OF POLYETHER IONOPHORE ANTIBIOTICS TO CONTROL BACTERIAL GROWTH IN SUGAR PRODUCTION

BACKGROUND OF THE INVENTION

This invention relates to the use of polyether ionophore antibiotics to control bacterial growth during sugar (sucrose) production. It can be used with a wide variety of feedstocks such as sugar beet juice, sugar cane juice, hydrolyzed grain (e.g., corn or wheat) or any other starch or sugar-containing material that can be used to produce simple sugars.

One of the key steps in sugar production is an extraction process where feedstock such as sugar beets or sugar cane is treated to extract sugar (as an aqueous solution referred to herein as "sweet juice'~) from the plant material. For instance, in the case of sugar beets, a diffusion process is commonly employed where the beets are soaked in warm water. This is typically-performed at about 70° C. under acid conditions (pH around 6) for a period of 1 to 2 hours. During that time, heat-tolerant bacteria can proliferate, feeding on sugar and thus reducing the amount that can ultimately be recovered and marketed. This negatively impacts plant productivity and is a significant problem for the industry. Sugar cane is commonly subjected to an extraction process involving milling in which similar problems are encountered.

The microcrganisms causing the problem are mostly gram positive bacteria that belong to the *lactobacillus* genus. *Streptococcus, bacillus., clostridium, leuconostoc* and *pediococcus* may also be present. In the past, formaldehyde has been used in an attempt to control bacterial growth, but this raises serious safety concerns.

This invention concerns a method for the production of sugar wherein a polyether ionophore antibiotic such as monensin, narasin, salinomycin, lasalocid, maduramycin or semduramycin is used to control or supress bacterial growth during the process. These compounds have good activity against gram positive bacteria and do not easily degrade over time or under high temperatures. This makes them attractive to the sugar industry because:

1. they remain active for many days under typical sugar plant operating conditions; and
2. they remain active at the high temperatures and acid pH used in the extraction step.

The bacterial population in the extraction bath is greatly reduced by the addition of a bacteriostatic or bactericidal concentration, for example 0.5 to 3.0 ppm, preferably 0.5 to 1.5 ppm, of a polyether ionophore such as monensin. This control greatly reduces the bacterial consumption of sugar leading to a significant improvement in plant productivity. Surprisingly, there are no detectable polyether residues in the final white sugar crystals. This result is particularly important because it makes the invention suitable for manufacture of food grade, white sugar crystals.

1. Field of the Invention

THE KEY STEPS IN SUGAR PRODUCTION

The 4 main steps performed in a typical sugar plant are described hereafter.

EXTRACTION

The purpose of this step is to extract the sugar from the feedstock. It yields a sweet juice with a pH of about 6 that is very susceptible to bacterial contamination. It also extracts water-soluble substances such as proteins which must be removed from the medium since they can hinder sugar crystallization.

PURIFICATION

Its purpose is to eliminate organic substances extracted with the sugar. It consists in adding a mixture of lime and water to the sweet juice and then sending through a flow of carbon dioxide to precipitate calcium as calcium carbonate. After filtration, one gets a clear juice, with little organic content other than sucrose.

CONCENTRATION

This clear juice, which is about 14% sugar, is heated and concentrated into a syrup with a sugar content comprised between 60% and 70% by weight.

CRYSTALLIZATION

This last step yields white sugar and a byproduct, molasses. It consists in concentrating further the syrup at 85° C. under vacuum to bring it beyond the saturation point of sucrose (in a state called "supersaturation"). Then, one introduces a small amount of sugar crystals (about 0.5 g) to trigger crystallization which spreads rapidly through the liquid, turning it into a mass of white sugar crystals bathing in a syrup colored by impurities. The white sugar crystals are separated by centrifugation, rinsed and dried.

This crystallization step is repeated twice on the non-crystallized syrup coming out of the centrifuge. The second and third time, it yields brown sugar that is not marketed. Instead, it is reinjected at the beginning of the crystallization phase with the syrup coming from the evaporation step to yield more valuable white sugar. Only white sugar is marketed.

After the third iteration, the dark, noncrystallized juice has become molasses. It contains about 50% sugar and 30% foreign matter that prevents further crystallization.

2. Description of a Preferred Embodiment

BRIEF DESCRIPTION OF THE DRAWING

The drawing depicts an example of a plant that processes 500 tons of sugar beets per hour.

DETAILED DISCLOSURE OF THE METHOD FOR THE PRODUCTION OF SUGAR

The process is described for a plant treating 500 tons of sugar beets per hour.

1. EXTRACTION

Operating conditions:

Temperature: 70° C.; pH=6; duration: 1–2 hours; process: continuous.

The extraction process uses a conveyor immersed in water. It is fed at one end with chopped beets and at the other with warm water to which various sugar-rich residues have been added for recycling. The beets move against the flow of water, so their sugar concentration declines as that of the water increases.

Sweet juice containing about 14% sugar (plus water-soluble proteins and other impurities) runs off from the end where fresh beets are added to the conveyor while spent beets (pulp) are evacuated from the other end. The 500 tons of beets processed per hour yield about 500 $m^3$ of sweet juice and 500 tons of pulp.

2. PURIFICATION

Operating conditions:

Temperature: 75° C.; pH=8.5; duration: 1 hour; process: continuous.

The sweet juice from the extraction step is passed into a vat where it is mixed with an aqueous suspension of lime (200 g of CaO per liter). A stream of carbon dioxide is blown into the vat causing calcium carbonate to precipitate taking along large molecules such as proteins that can interfere with crystallization.

The 500 $m^3$ of sweet juice processed per hour use about 30 $m^3$ of aqueous-lime suspension and yield about 500 $m^3$ of purified sweet juice.

3. CONCENTRATION

Operating conditions:

Temperature: declining from 130° C. to 85° C.; pH=8.5; process: continuous.

The purified sweet juice is boiled down. The 500 $m^3$ of sweet juice (14–16% sugar) processed per hour yield 110 $m^3$ of concentrated syrup (60–70% sugar).

4. CRYSTALLIZATION

The 100 $m^3$ of concentrated syrup are run through the various phases of the crystallization step during which another 106 $m^3$ of water are evaporated off. Finally, one ends up with 60 tons per hour of white sugar and 20 tons of molasses with a 50% sugar concentration.

KEY PROPERTIES OF POLYETHER IONOPHORE ANTIBIOTICS

Experiments were conducted with several polyether ionophore antibiotics such as monensin, lasalocid and salinomycin using sweet juice extracted from sugar beets. These experiments confirmed the existence of bacteriostatic and bactericidal concentrations which, for these molecules, can be as low as 0.5 ppm to 3.0 ppm. At bacteriostatic concentrations, the growth of the bacterial population is inhibited. At bactericidal concentrations, the bacterial population drops.

We also did sensitivity testing showing that polyether ionophore antibiotics are active against most bacteria commonly encountered in sugar plants. For instance. Table 1 shows the reduction in bacterial count observed 6 hours after treatment with 3.0 ppm of monensin.

TABLE 1

The impact of monensin on the bacterial count of various microorganisms

| | BACTERIAL COUNT | | |
|---|---|---|---|
| | at t = O | at t = 6h | Pct reduct. |
| *Lactobacillus plantarium* | $1.2 \times 10^8$ | $4.1 \times 10^5$ | −99.70 |
| *Lactobacillus fermentum* | $6.2 \times 10^8$ | $4.4 \times 10^4$ | −99.99 |
| *Lactobacillus vaccimostercus* | $2.8 \times 10^8$ | $2.1 \times 10^5$ | −99.90 |
| *Lactobacillus buchneri* | $5.5 \times 10^8$ | $3.0 \times 10^3$ | −99.99 |
| *Lactobacillus yamanashiensis* | $1.8 \times 10^5$ | $4.6 \times 10^4$ | −74.40 |
| *Lactobacillus coryniformis* | $3.7 \times 10^8$ | $3.3 \times 10^6$ | −99.10 |
| *Leuconostoc mesenteroides* | $8.0 \times 10^5$ | $5.4 \times 10^3$ | −99.30 |
| *Leuconostoc acidilactici* | $8.2 \times 10^8$ | $3.7 \times 10^8$ | −54.90 |
| *Bacillus subtills* | $3.1 \times 10^5$ | $5.5 \times 10^4$ | −82.30 |
| *Bacillus brevis* | $3.3 \times 10^8$ | $6.0 \times 10^3$ | −99.99 |
| *Bacillus megaterium* | $1.3 \times 10^8$ | $5.8 \times 10^7$ | −55.40 |
| *Bacillus coagulans* | $1.1 \times 10^5$ | $6.1 \times 10^4$ | −44.60 |

In addition, we observed that polyether ionophore antibiotics are stable at temperatures of about 70° C. and a pH of about 6, i.e. conditions similar to those encountered in extraction baths. They are thus active under normal plant operating conditions. They degrade partly however, at the higher temperatures encountered downstream from extraction, which helps to produce white sugar crystals free of monensin residues.

RESIDUE ANALYSIS

To ascertain that white sugar crystals were free of monensin residues, Trials were conducted with the help of the French Sugar Research Institute, an industry-funded research organization. All monensin assays were done by the European Institute for the Environment located in Bordeaux, France, a well-known independent lab using the officially approved assay method (H.P.L.C.).

MONENSIN IN THE PURIFICATION PHASE·

A master solution of monensin was first prepared by dissolving monensin crystals in 96% alcohol to reach a concentration of 20 g of monensin per liter of solution. Part of this solution was further diluted with water down to a concentration of 150 mg of monensin per liter. This was then used to supplement the sweet juice from extraction. Three different trials were made using varying concentrations of monensin in the sweet juice, i.e., 0.5 ppm, 1.0 ppm and 1.5 ppm.

The monensin-supplemented juice was then subjected to a typical purification step. Samples of 500 ml of filtered, purified juice were taken from the output stream immediately after filtration. They were assayed using the officially approved H.P.L.C. method. Results are summarized in the table below. They show that nearly 90% of monensin is eliminated by the purification step. This is understandable given monensints affinity for positive ions: it combines with calcium ion and is eliminated with it.

| MONENSIN CONTENT | | Percent of monensin eliminated by |
|---|---|---|
| before purification | after purification | purification |
| 0.5 | $<0.1$ | $>80$ |
| 1.0 | 0.13 | 87 |
| 1.5 | 0.17 | 89 |

MONENSIN IN THE CONCENTRATION PHASE

Purified juice from the purification step was first standardized to 14.7% dry matter by addition of distilled water. This standardized juice was then treated with 1.5 ppm of monensin using the 150 mg/l dilute alcohol solution prepared in the extraction step. The monensin containing juice was first heated to 120° C. for 10 minutes. The temperature was then lowered to 100° C. until the dry matter concentration reached about 61%. The syrup was assayed by H.P.L.C. and a monensin content of 2.2 ppm was measured.

This was less than could have been expected from the mere concentration of the juice. Indeed that concentration should have raised the monensin content from 1.5 ppm to 6.2 ppm. Since only 2.2 ppm were found, it means that the difference, i.e., 4 ppm or 64% of the original quantity introduced at the start of the experiment, was destroyed by heat.

MONENSIN IN THE CRYSTALLIZATION PHASE

Syrup from the concentration step was supplemented with 1.5 ppm of monensin using the dilute monensin-alcohol solution (150 mg/l) prepared in the extraction step. After the white sugar was crystallized, rinsed and dried, both the sugar and the remaining non-crystallized molasses were assayed. Results show:

No detectable amount of monensin in the white sugar (assay sensitivity: 0.5 ppm)

1.5 ppm in the remaining non-crystallized molasses

This shows that monensin stays in the liquid and that the rinsed white sugar crystals are free of monensin. Monensin ends up in the molasses instead.

ECONOMIC BENEFITS

The normal bacterial count in the extraction bath of a sugar plant is about $10^5$ to $10^6$ organisms/ml. Concern starts building above that and the contamination becomes significant when it reaches $10^9$/ml. These bacteria feed on sugar and lower the amount that is eventually recovered.

The chart here-below illustrates what happens when 1.5 ppm of monensin is introduced into the extraction juice. Most of it is destroyed along the way. The rest ends up in the molasses at a concentration of 2.6 ppm.

These calculations, however, assume a continuous usage of monensin in sugar production. In practice, the management of bacterial contamination require that the juice from extraction need only be treated one day per week to bring the bacterial count down to the no-problem zone until the next treatment. Under these conditions, the average monensin concentration in molasses would be 0.4 ppm.

This compares favorably with the 30 ppm of monensin that are commonly used to supplement beef feed rations and should not interfere with the use of molasses as animal feed.

I claim:

1. In a method of producing sugar comprising extraction of the sugar from a feedstock selected form the group consisting of sugar beet juice, sugar cane juice, hydrolyzed grain, and starch or sugar containing materials to yield a sweet juice, purification of the sweet juice to yield a clear juice, concentration of the clear juice, and crystallization of the sugar, the improvement comprising adding to said feedstock during said extraction a gram positive bacteria controlling or suppressing amount of one or more polyether ionophores to control or suppress bacterial growth during said method of producing sugar.

2. A method according to claim 1, wherein the polyether ionophore is added during extraction.

3. A method according to claim 2, wherein the amount of polyether ionophore added is from 0.5 to 3.0 ppm.

4. A method according to claim 3, wherein the amount of polyether ionophore is from 0.5 to 1.5 ppm.

5. A method according to claim 1, wherein the polyether ionophore is monensin, narasin, salynomycin, lasalocid, maduramycin, semduramycin, or a combination thereof.

6. A method according to claim 5, wherein the amount of polyether ionophore added is from 0.5 to 3.0 ppm.

7. A method according to claim 5, wherein the amount of polyether ionophore added is from 0.5 to 1.5 ppm.

8. A method according to claim 1, wherein the polyether ionophore is monensin.

9. A method according to claim 8, wherein the polyether ionophore is added during extraction.

10. A method according to claim 9, wherein the amount of polyether ionophore added is from 0.5 to 3.0 ppm.

11. A method according to claim 9, wherein the amount of polyether ionophore added is from 0.5 to 1.5 ppm.

* * * * *